(12) United States Patent
Kelley, Jr. et al.

(10) Patent No.: US 10,696,466 B2
(45) Date of Patent: Jun. 30, 2020

(54) CLEANING KIT

(71) Applicant: Berkshire Holding Corporation, Whitsett, NC (US)

(72) Inventors: Whitmore B Kelley, Jr., Lebanon, NH (US); Susan E Faile, Asheboro, NC (US); Justin J Autry, Durham, NC (US); David Capotosto, Biddeford, ME (US)

(73) Assignee: Berkshire Holding Corporation, Whitsets, NC (US)

( * ) Notice: Subject to any disclaimer, the term of this patent is extended or adjusted under 35 U.S.C. 154(b) by 0 days.

(21) Appl. No.: 16/081,177

(22) PCT Filed: Dec. 11, 2017

(86) PCT No.: PCT/US2017/655730
§ 371 (c)(1),
(2) Date: Aug. 30, 2018

(87) PCT Pub. No.: WO2018/107154
PCT Pub. Date: Jun. 14, 2018

(65) Prior Publication Data
US 2019/0023477 A1 Jan. 24, 2019

Related U.S. Application Data

(60) Provisional application No. 62/431,823, filed on Dec. 9, 2016.

(51) Int. Cl.
*B65D 81/32* (2006.01)
*B65D 75/54* (2006.01)
(Continued)

(52) U.S. Cl.
CPC .......... *B65D 81/3272* (2013.01); *A47L 13/10* (2013.01); *A47L 13/17* (2013.01);
(Continued)

(58) Field of Classification Search
CPC .......... A61L 2/18; B65D 25/08; B65D 71/08; B65D 75/30; B65D 75/38; B65D 75/54; B65D 81/32; B65D 81/3272
(Continued)

(56) References Cited

U.S. PATENT DOCUMENTS 5,814,159 A * 9/1998 Paley .................. A47K 10/32
134/6
5,988,371 A * 11/1999 Paley .................. A47K 10/32
206/229

(Continued)

OTHER PUBLICATIONS

PCT/US2017/065573 Search Report dated Mar. 8, 2018 Authorized officer Lee W. Young.

*Primary Examiner* — Bryon P Gehman
(74) *Attorney, Agent, or Firm* — MacCord Mason PLLC (57) ABSTRACT

The cleaning kit includes a first liquid-tight container and a second liquid-tight container adapted to be received within the first container to be ruptured by the application of pressure to the container by a user. The second container includes a sealable liquid-tight pouch; a baffle extending at least partially across the pouch adapted to reduce accidental rupture caused by handling during shipping and a frangible seal along at least a portion of an outer edge of the pouch. A cleaning liquid may be in the second container, wherein the second container is adapted to be openable while it is located in the first container to release the liquid from the second container into the first container. Also, there may be at least one absorbent applicator in the first container and adjacent to the second container in the first container whereby the release of cleaning liquid from the second container is applied to the applicators in the first container.

62 Claims, 9 Drawing Sheets

(51) Int. Cl.
 *C11D 17/04* (2006.01)
 *A47L 13/17* (2006.01)
 *A47L 13/10* (2006.01)
 *A61L 2/18* (2006.01)

(52) U.S. Cl.
 CPC ............ B65D 75/54 (2013.01); C11D 17/046 (2013.01); C11D 17/049 (2013.01); *A61L 2/18* (2013.01)

(58) Field of Classification Search
 USPC .................................................. 206/219–222
 See application file for complete search history.

(56) References Cited

U.S. PATENT DOCUMENTS

| | | | | |
|---|---|---|---|---|
| 6,068,820 | A | 3/2000 | De Guzman | 422/294 |
| 6,062,381 | A | 5/2000 | Paley et al. | 206/233 |
| 6,945,402 | B1 | 9/2005 | Gueret | 206/581 |
| 7,850,043 | B2 * | 12/2010 | Foster | B05B 11/0056 206/219 |
| 8,714,808 | B2 * | 5/2014 | Yamanaka | B65D 51/2821 206/222 |
| 9,440,779 | B1 | 9/2016 | Hach et al. | 75/527 |
| 9,743,803 | B2 * | 8/2017 | Foster | B65D 81/3211 |
| 2006/0124476 | A1 | 6/2006 | Sivakumar et al. | 206/207 |
| 2009/0044836 | A1 | 2/2009 | Bonnell et al. | 134/32 |
| 2009/0082743 | A1 | 3/2009 | Buglino et al. | 604/335 |
| 2014/0004227 | A1 | 1/2014 | Tran | 426/66 |

\* cited by examiner

CLEANING KIT

CROSS-REFERENCE TO RELATED APPLICATION

This application claims the priority of U.S. Provisional Patent Application Ser. No. 62/431,828, filed Dec. 9, 2016, which is hereby incorporated by reference in its entirety.

BACKGROUND OF THE INVENTIONS

(1) Field

The present inventions relate generally to cleaning devices and methods, and more particularly to such devices and methods used in cleaning "clean rooms", semiconductor fabrication plants, pharmaceutical manufacturing facilities, and other cleaning applications and environments where extreme cleanliness is maintained.

(2) Related Art

The requirements for maintaining cleanliness in semiconductor fabrication clean rooms, pharmaceutical manufacturing clean rooms and similar facilities are stringent. In semiconductor fabrication clean rooms, surfaces frequently must be wiped with an exceptionally clean wiper and cleaning solution in order to prevent contamination. The contamination which is to be controlled often is called "micro-contamination" because it consists of small physical contaminants, such as particulate matter of a size between that of bacteria and viruses, and chemical contaminants in very low concentrations, typically measured in parts per million or parts per billion.

The contaminants usually are of three types; particles, ions and non-volatile residues. These contaminants are deposited in the clean room and on products and surfaces to be cleaned by a host of sources including raw materials, previous processing steps, manufacturing equipment, and humans in the clean room. The wipers must be very clean to minimize the introduction of additional contaminants. Loose particles 100 micrometers and smaller in size are an anathema to obtaining high production yields and reliable semiconductor devices. Therefore, cleaning applicators and cleaning materials used in such clean rooms should emit as small a number of particles as possible. Similarly, contaminants interfere with the exacting processes of pharmaceutical and semiconductor manufacturing, and their quantities are to be minimized.

In the past, such requirements have been met by the provision of specially fabricated cloths designed to release very few loose particles, while maintaining structural integrity when wetted with cleaning solution and being used to wipe the surfaces to be cleaned. Typically, such wipers have been packaged in sealed containers such as flexible plastic bags, which can be opened, a wiper withdrawn and the bag resealed. Then, the cleaning solution, kept in a separate container, is applied to the wiper and the wiper is used.

Substantial quantities of chemical solvents used as cleaning fluids must be stored and applied to the wipers. This can result in accidents or working conditions deleterious to the health of the workers. Also, when workers apply cleaning fluids from separate containers to dry wiper cloths, the amount of cleaning fluid used often is either too little or too much, which can result in ineffective cleaning, or oversaturation and waste.

In response to these issues, pre-saturated wipers have been developed and commercialized. The wipers are pre-wetted with varying amounts of cleaning solutions, and packaged in a re-sealable plastic bag until needed. Then, the bag is opened, the wiper or wipers withdrawn, and the bag is re-closed. This is repeated until the bag is empty. Unfortunately, bags of pre-saturated wipers often may be stored for prolonged periods, such as months or even years before use. During that time, the cleaning liquid and the wiper material are in intimate contact with one another. It is believed that this often leads to a degradation of the fibers of the wiper material such that the quantity of contaminants released by the wiper when used is substantially higher than when the wipers are first packaged. It is believed that the bonds holding the particles to the fibers are loosened, and the releasable ions and extractables are increased by prolonged contact between the cleaning solutions and the wipers.

In addition, where adhesives are used to fasten various parts of plastic packaging together, such as in the re-closable seal of some wiper packages, the adhesive may deteriorate due to prolonged contact with the cleaning liquid.

Another issue of cleaning pharmaceutical manufacturing and other medical facilities with pre-saturated wipers lies in maintaining the effectiveness of the biocide. More specifically, the effectiveness of the biocide may deteriorate due to prolonged contact with the wiper material.

In order to overcome the various shortcomings of pre-saturated wipers, others have attempted to include both the unsaturated wipers and cleaning fluid in a single system, but with the wipers and cleaning fluid kept separate until immediately before use. One such system is set forth in U.S. Pat. No. 6,602,381 issued to Paley et al., the disclosure of which is hereby incorporated by reference in its entirety.

Challenges with these "point-of-use saturation" systems include leakage, bulky designs that are expensive to manufacture and ship, and difficulty in saturating the wipers with cleaning fluid prior to use. In particular, premature rupturing of the cleaning fluid compartment during shipping and handling is a serious problem, with known systems exhibiting a 40% failure rate when tested according to ASTM Test Protocol D5276-98 (2009) for Drop Test of Loaded Containers by Free Fall.

One way to protect against rupture during shipping is to employ bubble wrap or other special packaging to provide cushioning. Another way to protect against rupture during shipping is to minimize the quantity of packs in a shipped case in order to reduce weight and thus lessen the pressure on the contents when jostled during shipping. Unfortunately, cushioned packaging and/or shipping smaller quantities adds to shipping and materials expenses.

Another way to protect against rupture during shipping is to employ durable cleaning fluid packaging. Unfortunately, however, this durability likewise makes it difficult for the user to rupture the package in use. If the cleaning fluid packaging isn't effectively ruptured then the wipers may not be properly saturated.

Thus, there remains a need for a new and improved cleaning kit system including a first liquid-tight container that receives a second liquid-tight container and one or more applicators, the second liquid-tight container adapted to reduce accidental rupture during shipping and handling while, at the same time, being adapted to be easily ruptured by the application of pressure by a user to the first liquid-tight container.

SUMMARY OF THE INVENTIONS

The present inventions are directed to a cleaning kit including a first liquid-tight container and a second liquid-tight container adapted to be received within the first container, with the second liquid-tight container adapted to be ruptured by the application of pressure to the first liquid-tight container by a user. The second container includes a sealable liquid-tight pouch; a baffle extending at least partially across the pouch adapted to reduce accidental rupture caused by handling during shipping; and a frangible seal along at least a portion of an outer edge of the pouch, wherein the frangible seal is broken by the application of pressure greater than about 30 inches of water when tested according to ASTM Test F1140-07 (2007). A cleaning liquid is in the second container, wherein the second container is adapted to be openable while it is located in the first container to release the liquid from the second container into the first container. Also, there is at least one absorbent applicator in the first container and adjacent to the second container in the first container whereby the release of liquid from the second container is applied to the applicator in the first container.

The baffle may be selected from the group consisting of a partial weld line, a plurality of spaced apart dash weld lines, weld lines scattered and/or at angles to each other, a plurality of spaced apart weld dots, knurled seams, a plurality of intersecting weld lines, a plurality of spaced weld lines, one or more curved weld lines, and combinations thereof. Also, the welds may be formed by joining together opposite faces of the pouch by heat sealing, RF welding, ultrasonic welding, adhesives, and combinations thereof.

The baffle may be discontinuous in use. For example, in one embodiment the baffle partially extends across a portion of the pouch. In another embodiment, the baffle extends fully across the pouch and is adapted to be ruptured by the application of pressure to the container during shipping or in use by a user.

In one embodiment, the pouch is formed by sealing at least a pair of opposing edges of sheets of material and at least a portion of the sealed edge of the pouch is a frangible seal. The top edge of the pouch may include the frangible seal that is created after the container is filled with a liquid. Also, the pouch may be a fold pouch and at least a portion of one of the sealed edges of the fold pouch is a frangible seal.

Other pouch configurations within the scope of this invention include two pieces of film sealed on four sides; tubular film sealed on two sides; or one piece of folded film sealed on three sides. At least a portion of one of the seals on any of these configurations would be frangible.

In one embodiment, the baffle is adapted to provide an effective volume after filing with a liquid of between about 30% and about 80% and the strength of the frangible seal is between about 30 inches of water and about 80 inches of water when tested according to ASTM test F1140-07 (2007).

In another embodiment, the baffle is adapted to provide an effective volume after filing with a liquid of between about 40% and about 70% and the strength of the frangible seal is between about 40 inches of water and about 70 inches of water when tested according to ASTM test F1140-07 (2007).

In another embodiment, the baffle is adapted to provide an effective volume after filing with a liquid of between about 30% and about 65% and the strength of the frangible seal is between about 45 inches of water and about 65 inches of water when tested according to ASTM test F1140-07 (2007).

In still another embodiment, the baffle is adapted to provide an effective volume after filling with a liquid of about 60% and the strength of the frangible seal is about 55 inches of water when tested according to ASTM test F1140-07 (2007).

The applicator may be selected from the group consisting of wipers, mops, swabs, gloves, mitts, pads and combinations thereof. In one embodiment, the applicator is a wiper for use in clean rooms requiring the use of wipers producing very small quantities of contaminants in use. The applicator may include a plurality of the wipers forming a stack. Also, the applicator may be made from materials selected from the group consisting of knitted fabrics, woven fabrics, non-woven fabrics, foams, meshes, sponges and combinations thereof.

In one embodiment, the first liquid-tight container is a pouch having an opening for receiving the second liquid-tight container. The pouch may be a fold pouch formed from a single sheet of material having the edges joined together to form sides and the opening. The pouch may also be a 3-side sealed pouch formed from two sheets of material having the edges joined together to form sides and the opening.

In one embodiment, the opening of the pouch is sealable across the opening after receiving the second liquid-tight container. The pouch may be re-sealable after opening the first container during use. In one embodiment, the pouch is a re-sealable peel and re-seal pouch. In another embodiment, the pouch may further include a flap normally covering the opening and a pressure sensitive adhesive adapted to re-seal the first container after opening. In another embodiment, the pouch includes a re-sealable slider zipper adapted to re-seal the first container after opening. In still another embodiment, the pouch includes a re-sealable pressure zipper adapted to re-seal the first container after opening. Slider and pressure zippers are preferably located on a seam, versus on the top surface.

The pouch may be formed from a plastic film. In one embodiment, the plastic film is a single layer plastic film. In another embodiment, the plastic film is a multilayer, composite plastic film. The plastic film may be a thermoplastic film.

Accordingly, one aspect of the present inventions is to provide a cleaning kit, the kit including (a) a first liquid-tight container; (b) a second liquid-tight container adapted to be received within the first container, the second container having a baffle adapted to reduce accidental rupture caused by handling during shipping; and (c) a cleaning liquid in the second container, wherein the second container is adapted to be openable while it is located in the first container thereby releasing the liquid from the second container into the first container.

Another aspect of the present inventions is to provide an improved liquid container adapted to be ruptured by the application of pressure to the container by a user, the container including (a) a liquid-tight pouch; (b) a baffle adapted to reduce accidental rupture caused by handling during shipping extending at least partially across the pouch; and (c) a frangible seal along at least a portion of an outer edge of the pouch, wherein the frangible seal is broken by the application of pressure by a user to the container greater than about 30 inches of water when tested according to ASTM Test F1140-07 (2007).

Still another aspect of the present inventions is to provide a cleaning kit, the kit including (a) a first liquid-tight container; (b) a second liquid-tight container adapted to be received within the first container and ruptured by the application of pressure to the container by a user, the second container including (i) a sealable liquid-tight pouch; (ii) a baffle extending at least partially across the pouch adapted to reduce accidental rupture caused by handling during shipping and (iii) a frangible seal along at least a portion of an outer edge of the pouch, wherein the frangible seal is broken by the application of pressure to the second container by a user greater than about 30 inches of water when tested according to ASTM Test F1140-07 (2007); (c) a cleaning liquid in the second container, wherein the second container is adapted to be openable while it is located in the first container to release the liquid from the second container into the first container; and (d) at least one absorbent applicator in the first container and adjacent to the second container in the first container whereby the release of liquid from the second container is applied to the applicator in the first container.

These and other aspects of the present inventions will become apparent to those skilled in the art after a reading of the following description of embodiments when considered with the drawings.

BRIEF DESCRIPTION OF THE DRAWINGS

FIG. 5 depicts a method according to the present inventions including:

DESCRIPTION OF THE EMBODIMENTS

In the following description, like reference characters designate like or corresponding parts throughout the several views. Also in the following description, it is to be understood that such terms as "forward," "rearward," "left" "right," "upwardly," "downwardly," and the like are words of convenience and are not to be construed as limiting terms.

Figure 1:
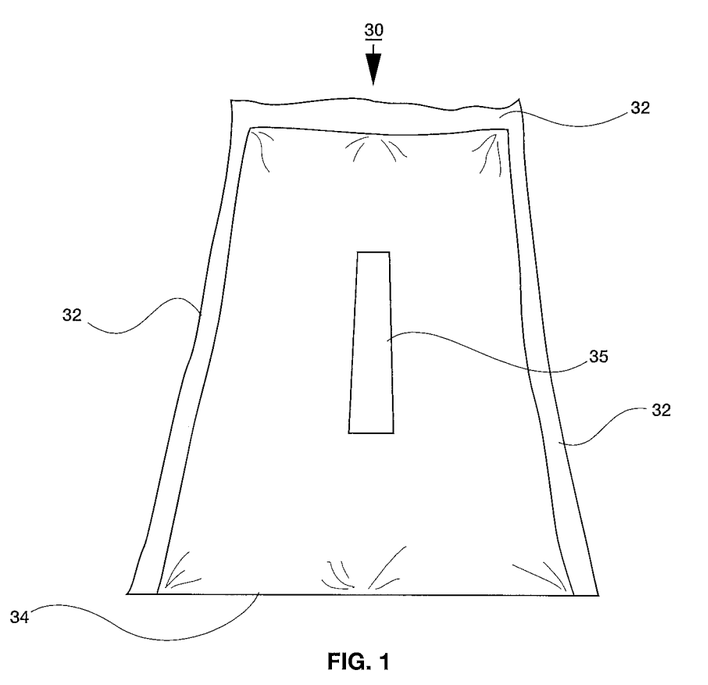
FIG. 1 is a perspective view of an inner container having a single baffle constructed according to the present inventions.

Referring now to the drawings in general and FIG. 1 in particular, it will be understood that the illustrations are for the purpose of describing a preferred embodiment of the inventions and are not intended to limit the inventions thereto. As best seen in FIG. 1, an inner liquid tight, second container 30 for the cleaning kit system, generally designated 10 in subsequent figures, is shown constructed according to the present inventions.

Container 30 is preferably a four-sided pouch having three frangible seams 32 and one folded edge 34, although other configurations are within the scope of this invention. As used herein, "frangible seam", "frangible seal" and the like shall refer to a seam that purposefully comes apart when a pre-determined amount of pressure is applied, rather than deforming elastically and retaining its cohesion as a single object. When force is applied to second container 30, for example through a user exerting pressure on first container 30, at least one frangible seam 32 is compromised and cleaning liquid is evacuated from container through broken frangible seam. It should be understood that it is not necessary that all frangible seams, in their entirety, be compromised. Rather, a portion of one seam compromised may be adequate to allow evacuation of cleaning liquid from second container.

Second container 30 is preferably formed of a piece of plastic film that is folded over and frangibly sealed along three edges. This film is preferably a liquid impermeable thermoplastic. Examples of suitable films include polyester, polypropylene, polyethylene, polyimide, TTFE, or laminates or coforms thereof.

Figure 2:
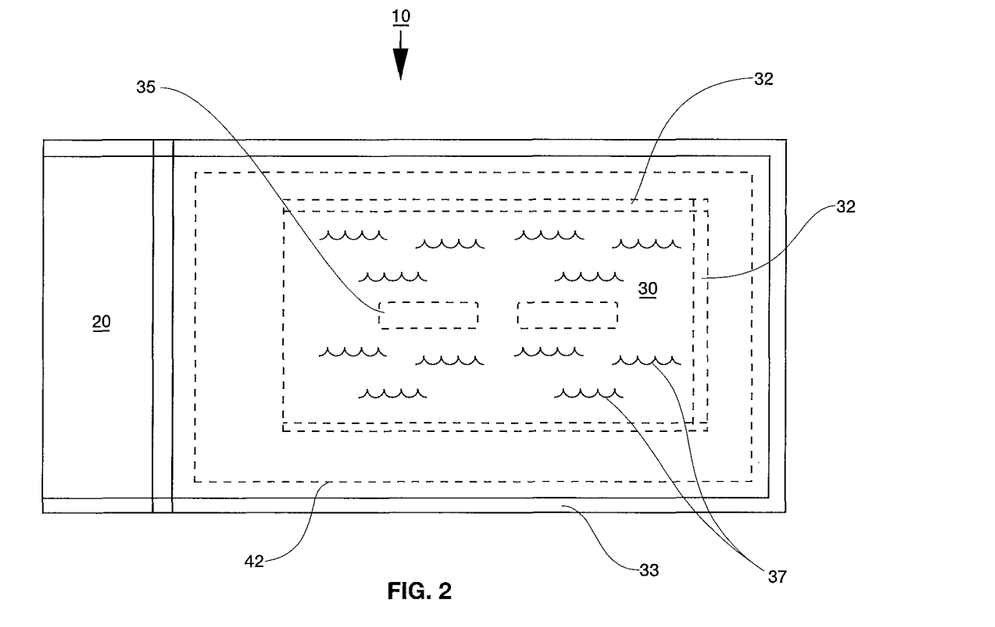
FIG. 2 is a top view of a cleaning kit showing internal components in phantom.

Second container 30 envelops a volume of cleaning fluid liquid 37 within, as shown in FIG. 2. As used herein, "cleaning fluid" shall refer to a wide variety of cleaning liquids including water, deionized water, organic solvents, soaps, surfactants, degreasers, biocides, alcohols, hydrogen peroxide, sodium hypochlorite, ammonia, sodium hydroxide, acids, and mixtures thereof.

Figure 3:
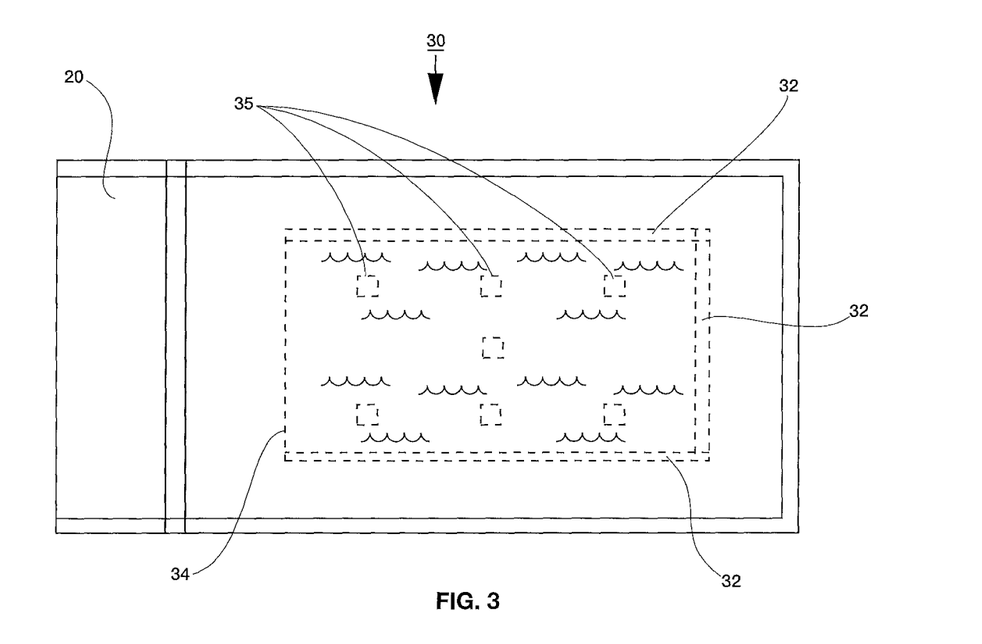
FIG. 3 is a top view of a cleaning kit with an inner bag having a plurality of baffles.

Second container 30 contains at least one baffle 35, but two baffles, or a plurality of baffles, as shown in FIGS. 2 and 3 respectively, are also within the scope of the present inventions. Baffles 35 are preferably formed by welding the two sides of film together, optionally with the resulting baffle seal being slightly weaker than the frangible seam 32. Said another way, when pressure is applied to second container 30, the baffle weld will give way before frangible seams give way. Thus, the "rupturing" event of the second container can typically occur in two parts: the baffle weld or portion thereof will come apart, then the frangible seal will give way and allow the liquid to escape. Baffles may be oriented in a variety of ways including a partial weld line, a plurality of spaced apart dashed weld lines, weld lines scattered and/or at angles to each other, a plurality of spaced apart weld dots, knurled seams, a plurality of intersecting weld lines, a plurality of spaced weld lines, one or more curved weld lines, and combinations thereof. Baffles may be formed by joining together opposite faces of the inner container by means such as heat sealing, RF welding, ultrasonic welding, adhesive, and combinations thereof.

It is desirable that the baffle is "discontinuous in use". As use herein, "discontinuous in use" shall mean that the baffle doesn't significantly impede the movement of flow within the second container when the frangible seam of the second container is compromised. Said another way, if in use a user applies pressure to the second container so the baffles and frangible seams "give way", the baffles that have "given way" can't significantly prevent the cleaning fluid liquid from draining out of the second container through broken frangible seam. Likewise if baffles are designed to remain intact during rupturing of frangible seam(s), the baffles can't be oriented in a manner that would prevent evacuation of virtually all of the cleaning fluid liquid from the second container when the frangible seams have given way. A discontinuous baffle can extend only partially across a portion of the inner container, or extend fully across the inner container.

Figure 4:
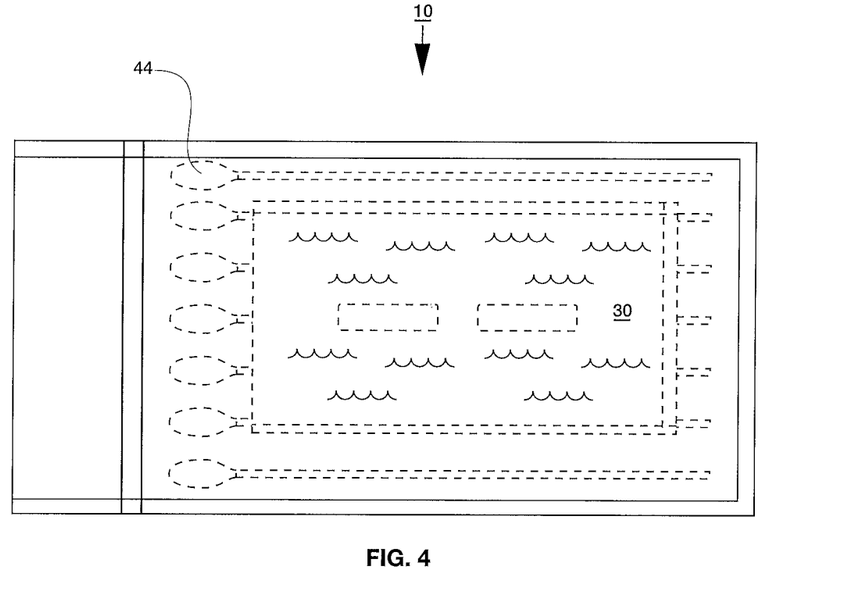
FIG. 4 is a top view of a cleaning kit with swabs.

As shown in FIG. 2, cleaning kit 10 includes second container 30, and at least one wiper 42, within first container 20. While wiper 42 is generally used herein for conciseness, it should be understood that the present inventions pertain to a cleaning kit having a variety of cleaning applicators 40 including mops 43, swabs 44 (FIG. 4), gloves 45, mitts 46 and pads 47, in addition to wipers 42. Applicators can be constructed of a variety of materials including knitted fabrics, woven fabrics, non-woven-fabrics, foams, meshes, sponges and combinations thereof. Wipers may be very low quantity contaminant wipers approved for use as clean room wipers in accordance with IEST-RP.CC004.3. One cleaning kit may contain more than one type of cleaning applicators. Cleaning applicators 40 may be provided singly or as a plurality in each first container. Where a plurality of cleaning applicators are provided, a specific configuration may be preferred, for example a stack of wipes. Applicators are preferably absorbent with respect to the cleaning fluid liquid.

First container 20 is preferably constructed of a liquid impermeable plastic film such as laminated PET/LLDPE film, or PET, PA, PP, CoPET variations, that is preferably sealed on peripheral edges with standard (non-frangible) seam 33. Preferably, the plastic film is a thermoplastic. The plastic film may be a multilayer composite plastic film. In one embodiment, first container 20 is formed from a piece of plastic film having its outer edges joined together, and including an opening to form a pouch through which second container 30 is inserted. Alternatively, first container 20 can be formed of two sheets of material having joined edges. First container 20 preferably includes access opening 22 (FIG. 5D) through which cleaning applicators 40 may be removed. FIG. 5 will be discussed in more detail infra.

Opening 22 is preferably closed using seal 23. Seal 23 can be a variety of configurations including re-sealable "peel and seal" flaps, pressure sensitive adhesives, slider zippers, and combinations thereof. Opening 22 can preferably be opened and reclosed using seal 23 multiple times. Second container 30 is enclosed within first container 20.

The effective volume of cleaning fluid liquid within the second container is a crucial aspect of the present inventions. If the effective volume is too low, then it is difficult for the user to rupture the inner container for use. Too low volumes will also result in more time required to achieve uniform saturation and may limit the number of wipers in the pack for a desired saturation level. If the effective volume is too high, then the second container is likely to rupture before desired, for example during shipping. As used herein "effective volume" shall refer to the maximum volume of fluid in a baffled container versus the maximum volume of fluid in that container without a baffle, expressed as a percentage. By way of example, if a 1 liter container with baffles has a maximum volume of 0.7 liters, the effective volume would be 70%. This is calculated as follows:

$(V_{Baffle}/V_{Unbaffled}) \times 100 = $ Effective Volume

Likewise, the strength of frangible seam 32 is an aspect of the present inventions. If the frangible seam is too strong then it is difficult for the user to rupture the inner container for use, but if it is too weak then the second container is likely to prematurely rupture.

Extensive experimentation was necessary to achieve both ease of use and shipping and handling durability. "Ease of use" pertains to how easy it is for a user, for example a cleaning technician in a clean room, to rupture the second container for purposes of allowing cleaning fluid liquid to come in contact with cleaning applicator. "Shipping durability" refers to how resilient the second container is during the shipping and handling process, as defined by ASTM Test Protocol D5276-98 (2009) for Drop Test of Loaded Containers by Free Fall. Ease of use and shipping durability are inherently contradictory qualities.

Figure 6:
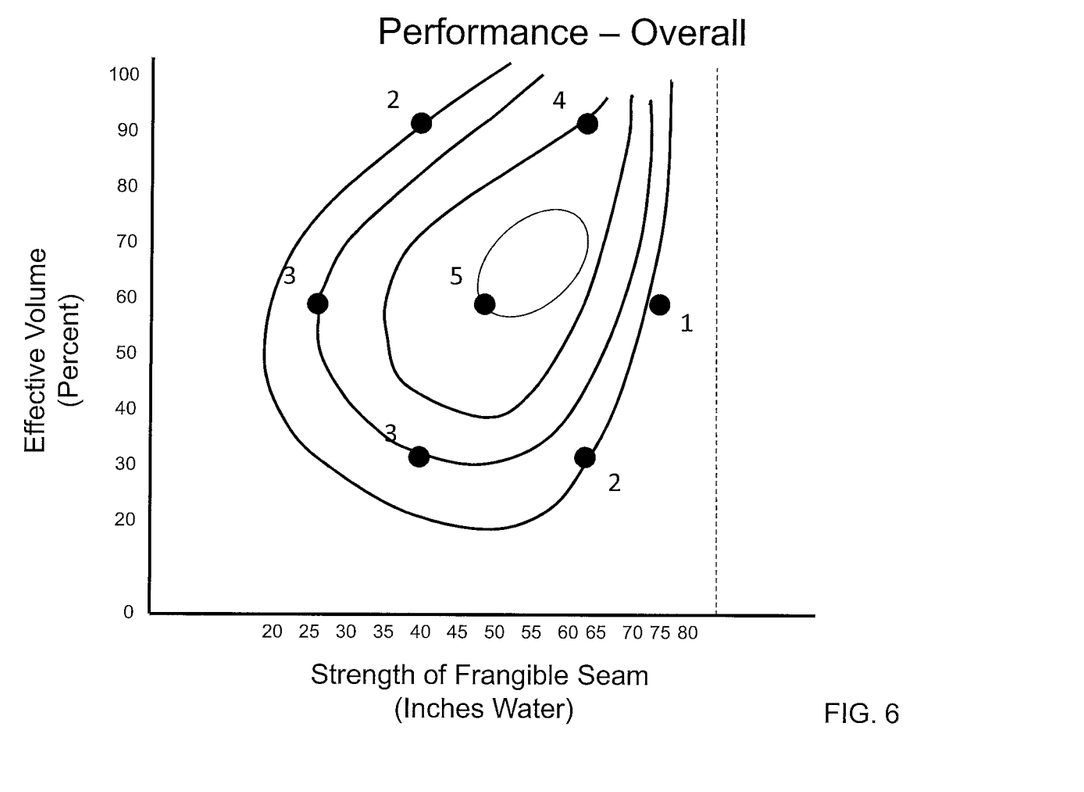
FIG. 6 is a contour plot of a response surface graphically illustrating overall performance of ease of opening and shipping and handling durability on a scale of 1-5 as a function of the effective volume of the liquid inner container and the strength of the frangible seal.

FIG. 6 quantifies overall performance on a 1-5 scale, with 5 being the best.

It should be understood that the addition of baffles is a critical element of the invention insofar as it permits both ease of use and shipping durability. Previous technologies optimized one at the expense of the other.

It is desirable that the inner container of the present inventions has an effective volume of approximately 30%-80%, and a frangible seam strength of approximately 30-80 inches of water. It is more desirable that the inner container of the present inventions has an effective volume of approximately 40%-70%, and a frangible seam strength of approximately 40-70 inches of water. It is even more desirable that the inner container of the present inventions has an effective volume of approximately 45%-65%, and a frangible seam strength of approximately 45-65 inches of water. It is most desirable that the inner container of the present inventions has an effective volume of approximately 60%, and a frangible seam strength of approximately 55 inches of water. As used herein, frangible seal strength is determined by ASTM Protocol F1140-07 (2007).

As demonstrated in the following prophetic tables, the percent of pouch volume capacity is also an important factor in performance. In these tables a rating of 1 is unacceptable; 2 is a 10% failure rate; 3 is a 1% failure rate; 4 is a <0.023% failure rate; and 5 is excellent performance. As used herein "percent of pouch volume capacity" shall refer to the percent capacity that a pouch is filled. For example, if a baffled or unbaffled pouch has a maximum capacity of 1 liter, but is filled with 0.8 liters, the percent of pouch volume capacity would be 80%. This is calculated as followed:

$(V_{Actual}/V_{Capacity}) \times 100 = $ Percent of Pouch Volume Capacity

TABLE 1

| | | Effective Point of Use Bursting | | | | | | |
|---|---|---|---|---|---|---|---|---|
| | | Frangible Pouches NO Baffles Effective Point of Use Bursting | | | | Frangible Pouches With Baffles Effective Point of Use Bursting | | |
| % of Pouch Volume capacity | 90 | 5 | 5 | 2 | 90 | 5 | 5 | 2 |
| | 60 | 5 | 5 | 1 | 60 | 5 | 5 | 1 |
| | 30 | 3 | 2 | 1 | 30 | 3 | 3 | 1 |
| | | 25 | 50 | 75 | | 25 | 50 | 75 |
| | | Frangible Seal Strength [in/H$_2$O] | | | | Frangible Seal Strength [in/H$_2$O] | | |

TABLE 2

Ability to Withstand Shipping (ASTM D5276-98 (2009))

| | | Frangible Pouches NO Baffles Durability | | | | Frangible Pouches With Baffles Durability | | |
|---|---|---|---|---|---|---|---|---|
| % of Pouch Volume Capacity | 90 | 1 | 1 | 4 | 90 | 2 | 5 | 4 |
| | 60 | 1 | 1 | 5 | 60 | 3 | 5 | 5 |
| | 30 | 3 | 3 | 5 | 30 | 4 | 5 | 5 |
| | | 25 | 50 | 75 | | 25 | 50 | 75 |
| | | Frangible Seal Strength [in/H$_2$O] | | | | Frangible Seal Strength [in/H$_2$O] | | |

TABLE 3

Overall Performance (Lowest Value of First Two Charts)

| | | Frangible Pouches NO Baffles Overall Performance | | | | Frangible Pouches With Baffles Overall Performance | | |
|---|---|---|---|---|---|---|---|---|
| % of Pouch Volume Capacity | 90 | 1 | 1 | 2 | 90 | 2 | 5 | 2 |
| | 60 | 1 | 1 | 1 | 60 | 3 | 5 | 1 |
| | 30 | 3 | 2 | 1 | 30 | 3 | 3 | 1 |
| | | 25 | 53 | 75 | | 25 | 50 | 75 |
| | | Frangible Seal Strength [in/H$_2$O] | | | | Frangible Seal Strength [in/H$_2$O] | | |

Figure 5A:
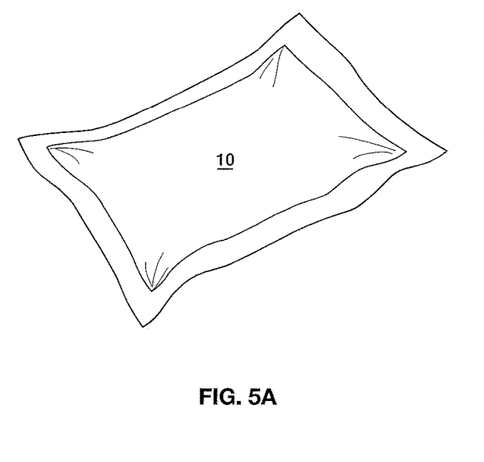
FIG. 5A showing a cleaning kit.
Figure 5B:
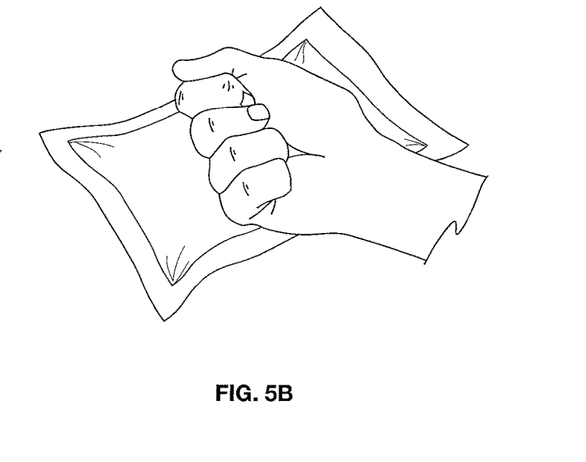
FIG. 5B depicting a user applying pressure to an outer container.
Figure 5C:
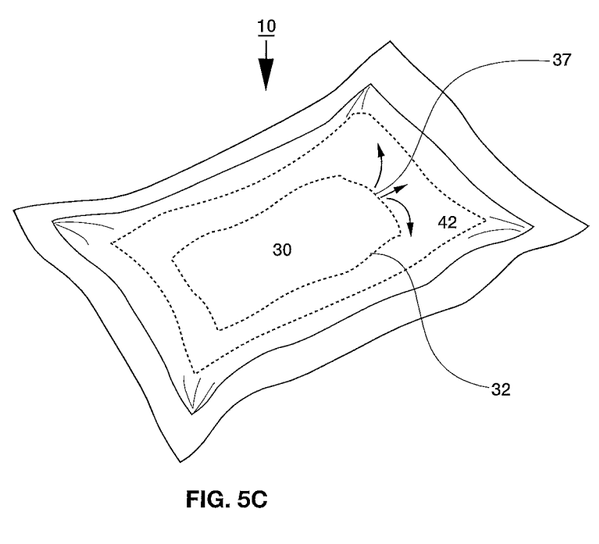
FIG. 5C showing cleaning liquid escaping from a broken frangible seam.
Figure 5D:
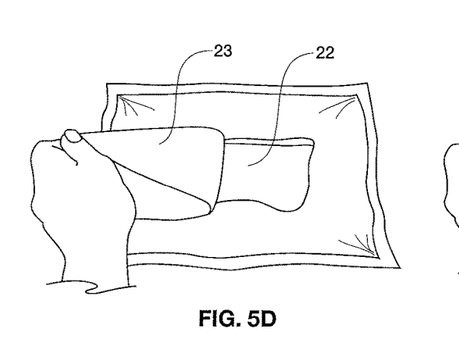
FIG. 5D depicting a user opening an outer container.
Figure 5E:
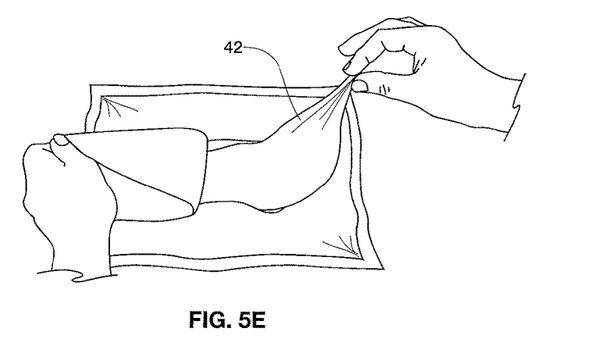
FIG. 5E showing a user removing a single wiper.
Figure 5F:
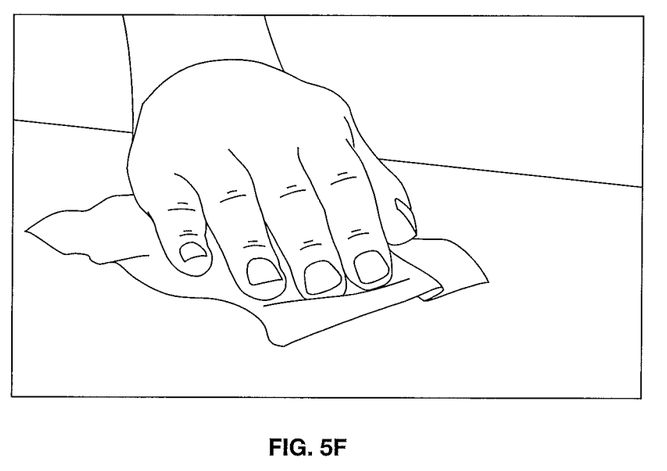
FIG. 5F showing a user wiping a surface with a wiper.

Referring now back to FIG. 5, FIG. 5A depicts the cleaning kit having a second container 30 enclosing a volume of cleaning fluid, and at least one cleaning applicator 42. FIG. 5B depicts a user applying force to the cleaning kit for purposes of rupturing second container 30 to release cleaning liquid into the first container 20. It should be understood that the application of force can be achieved by a variety of methods including folding, striking, twisting, and pushing the cleaning kit with hands, other objects, or a combination. Also, it should be understood that pressure is exerted on first container 20, and that force carries through to second container 30. The user doesn't open first container 20 to access and apply pressure to second container 30. FIG. 5C depicts cleaning liquid 37 escaping frangible seam 32 of second container 30, where it would come in contact with wiper 42 within first container 20. FIG. 5D depicts a user peeling back seal 23 to reveal access opening 22. FIG. 5E depicts a user removing a wiper 42. FIG. 5F depicts a user wiping a surface with a wiper.

Certain modifications and improvements will occur to those skilled in the art upon a reading of the foregoing description. By way of example, baffles could be structures other than welds, for example physical barriers such as flaps, objects, gussets, folds, and combinations thereof. Also, the second pouch could be fixed to the first pouch on one or more sides so that the second pouch can't move or shift relative to the first pouch or be accidentally removed from the first pouch. It should be understood that all such modifications and improvements have been deleted herein for the sake of conciseness and readability but are properly within the scope of the following claims. It should also be understood that "approximately" and other similar terms are +/−10% unless otherwise stated or contrary to common sense. All ranges set forth should be understood to include stated endpoints as well as all increments there between. It should be understood that all such modifications and improvements have been deleted herein for the sake of conciseness and readability but are properly within the scope of the following claims.

We claim:

1. A cleaning kit, said kit comprising:
   (a) a first liquid-tight container;
   (b) a second liquid-tight container adapted to be received within said first container, said second container having a baffle adapted to reduce accidental rupture caused by handling during shipping;
   (c) a cleaning liquid in said second container, wherein said second container is adapted to be openable while it is located in said first container to release said cleaning liquid from said second container into said first container; and
   (d) a frangible seal along at least a portion of an outer edge of said second liquid tight container, wherein said frangible seal is broken by the application of pressure to said second container by a user greater than about 30 inches of water when tested according to ASTM Test F1140-07 (2007).

2. The cleaning kit according to claim 1 further including at least one absorbent applicator in said first container.

3. The cleaning kit according to claim 2, wherein said at least one absorbent applicator is selected from the group consisting of wipers, mops, swabs, gloves, mitts, pads and combinations thereof.

4. The cleaning kit according to claim 3, wherein said at least one absorbent applicator is a wiper for use in clean rooms requiring the use of wipers producing very small quantities of contaminants in use.

5. The cleaning kit according to claim 4, wherein said at least one absorbent applicator includes a plurality of said wipers forming a stack.

6. The cleaning kit according to claim 4, wherein said at least one absorbent applicator is made from materials selected from the group consisting of knitted fabrics, woven fabrics, non-woven fabrics, foams, meshes, sponges and combinations thereof.

7. The cleaning kit according to claim 1, wherein said first liquid-tight container is a pouch having an opening for receiving said second liquid-tight container.

8. The cleaning kit according to claim 7, wherein said pouch is a fold pouch formed from a single sheet of material having the edges joined together to form sides and said opening.

9. The cleaning kit according to claim 7, wherein said pouch is a 3-side sealed pouch formed from two sheets of material having the edges joined together to form sides and said opening.

10. The cleaning kit according to claim 7, wherein the opening of said pouch is sealable across said opening after receiving said second liquid-tight container.

11. The cleaning kit according to claim 7, wherein said pouch is re-sealable after opening said first container during use.

12. The cleaning kit according to claim 11, wherein said pouch is a re-sealable peel and seal pouch.

13. The cleaning kit according to claim 11, wherein said pouch further includes a flap normally covering said opening and a pressure sensitive adhesive adapted to re-seal said first container after opening.

14. The cleaning kit according to claim 11, wherein said pouch includes a re-sealable slider zipper adapted to re-seal said first container after opening.

15. The cleaning kit according to claim 11, wherein said pouch includes a re-sealable pressure zipper adapted to re-seal said first container after opening.

16. The cleaning kit according to claim 7, wherein said pouch is formed from a plastic film.

17. The cleaning kit according to claim 16, wherein said plastic film is a single layer plastic film.

18. The cleaning kit according to claim 16, wherein said plastic film is a multilayer, composite plastic film.

19. The cleaning kit according to claim 16, wherein said plastic film is a thermoplastic film.

20. An improved liquid container adapted to be ruptured by the application of pressure to said container by a user, said container comprising:
(a) a liquid-tight pouch;
(b) a baffle extending at least partially across said pouch adapted to reduce accidental rupture caused by handling during shipping; and
(c) a frangible seal along at least a portion of an outer edge of said pouch, wherein said frangible seal is broken by the application of pressure to said container by a user greater than about 30 inches of water when tested according to ASTM Test F1140-07 (2007).

21. The container according to claim 20, wherein said baffle is selected from the group consisting of a partial weld line, a plurality of spaced apart dash weld lines, a plurality of scattered weld lines, a single weld dot, a plurality of spaced apart weld dots, a single knurled seam, a plurality of knurled seams, a plurality of intersecting weld lines, and combinations thereof.

22. The container according to claim 21, wherein said baffle is formed by joining together opposite faces of said pouch by one of heat sealing, RE welding, ultrasonic welding, adhesives or combinations thereof.

23. The container according to claim 20, wherein said baffle is discontinuous in use.

24. The container according to claim 23, wherein said baffle partially extends across a portion of said pouch.

25. The container according to claim 23, wherein said baffle extends fully across said pouch and said baffle is adapted to be ruptured by the application of pressure by a user to said container.

26. The container according to claim 20, wherein said pouch is a pouch formed by sealing at least pair of opposing edges of sheets of material and at least a portion of a sealed edge of said pouch is a frangible seal.

27. The container according to claim 26, wherein a top edge of said pouch includes a top edge frangible seal that is created after said container is filled with a liquid.

28. The container according to claim 26, wherein said pouch is a fold pouch and at least a portion of a sealed edge of said fold pouch is a frangible seal.

29. The container according to claim 20, wherein said baffle is adapted to provide an effective volume after filling with a liquid of between about 30% and about 80% and the strength of said frangible seal is between about 30 inches of water and about 80 inches of water when tested according to ASTM test F1140-07 (2007).

30. The container according to claim 29, wherein said baffle is adapted to provide an effective volume after filling with a liquid of between about 40% and about 70% and the strength of said frangible seal is between about 40 inches of water and about 70 inches of water when tested according to ASTM test F1140-07 (2007).

31. The container according to claim 30, wherein said baffle is adapted to provide an effective volume after filling with a liquid of between about 30% and about 65% and the strength of said frangible seal is between about 45 inches of water and about 65 inches of water when tested according to ASTM test F1140-07 (2007).

32. The container according to claim 30, wherein said baffle is adapted to provide an effective volume after filling with a liquid of about 60% and the strength of said frangible seal is about 55 inches of water when tested according to ASTM test F1140-07 (2007).

33. A cleaning kit, said kit comprising:
(a) a first liquid-tight container;
(b) a second liquid-tight container adapted to be received within said first container, said second container to be ruptured by the application of pressure to said first container by a user, said second container including (i) a sealable liquid-tight pouch; (ii) a baffle extending at least partially across said pouch adapted to reduce accidental rupture caused by handling during shipping and (iii) a frangible seal along at least a portion of an outer edge of said pouch, wherein said frangible seal is broken by the application of pressure to said second container by a user greater than about 30 inches of water when tested according to ASTM Test F1140-07 (2007);
(c) a cleaning liquid in said second container, wherein said second container is adapted to be openable while it is located in said first container to release said liquid from said second container into said first container; and
(d) at least one absorbent applicator in said first container and adjacent to said second container in said first container whereby the release of liquid from the second container is applied to said at least one absorbent applicator in said first container.

34. The cleaning kit according to claim 33, wherein said at least one absorbent applicator is selected from the group consisting of wipers, mops, swabs, gloves, mitts, pads and combinations thereof.

35. The cleaning kit according to claim 34, wherein said at least one absorbent applicator is a wiper for use in clean rooms requiring the use of wipers producing very small quantities of contaminants in use.

36. The cleaning kit according to claim 35, wherein said at least one absorbent applicator includes a plurality of said wipers forming a stack.

37. The cleaning kit according to claim 35, wherein said at least one absorbent applicator is made from materials selected from the group consisting of knitted fabrics, woven fabrics, non-woven fabrics, foams, meshes, sponges and combinations thereof.

38. The cleaning kit according to claim 33, wherein said first liquid-tight container is a pouch having an opening for receiving said second liquid-tight container.

39. The cleaning kit according to claim 38, wherein said pouch is a fold pouch formed from a single sheet of material having the edges joined together to form sides and said opening.

40. The cleaning kit according to claim 38, wherein said pouch is a 3-side sealed pouch formed from two sheets of material having the edges joined together to form sides and said opening.

41. The cleaning kit according to claim 38, wherein the opening of said pouch is sealable across said opening after receiving said second liquid-tight container.

42. The cleaning kit according to claim 38, wherein said pouch is re-sealable after opening said first container during use.

43. The cleaning kit according to claim 42, wherein said pouch is a re-sealable peel and seal pouch.

44. The cleaning kit according to claim 42, wherein said pouch further includes a flap normally covering said opening and a pressure sensitive adhesive adapted to re-seal said first container after opening.

45. The cleaning kit according to claim 42, wherein said pouch includes a re-sealable slider zipper adapted to re-seal said first container after opening.

46. The cleaning kit according to claim 42, wherein said pouch includes a re-sealable pressure zipper adapted to re-seal said first container after opening.

47. The cleaning kit according to claim 38, wherein said pouch is formed from a plastic film.

48. The cleaning kit according to claim 47, wherein said plastic film is a single layer plastic film.

49. The cleaning kit according to claim 47, wherein said plastic film is a multilayer, composite plastic film.

50. The cleaning kit according to claim 47, wherein said plastic film is a thermoplastic film.

51. The container according to claim 33, wherein said baffle is selected from the group consisting of a partial weld line, a plurality of spaced apart dash weld lines, a plurality of scattered weld lines, a single weld dot, a plurality of spaced apart weld dots, a single knurled seam, a plurality of knurled seams, a plurality of intersecting weld lines, and combinations thereof.

52. The container according to claim 51, wherein said baffle is formed by joining together opposite faces of said pouch by one of heat sealing, RF welding, ultrasonic welding, adhesives or combinations thereof.

53. The container according to claim 33, wherein said baffle is discontinuous in use.

54. The container according to claim 53, wherein said baffle partially extends across a portion of said pouch.

55. The container according to claim 53, wherein said baffle extends fully across said pouch and is adapted to be ruptured by the application of pressure to said container during shipping or in use by a user.

56. The container according to claim 33, wherein said pouch is a pouch formed by sealing at least pair of opposing edges of sheets of material and at least a portion of a sealed edge of said pouch is a frangible seal.

57. The container according to claim 56, wherein a top edge of said pouch includes a top edge frangible seal that is created after said container is filled with a liquid.

58. The container according to claim 56, wherein said pouch is a fold pouch and at least a portion of a sealed edge of said fold pouch is a frangible seal.

59. The container according to claim 33, wherein said baffle is adapted to provide an effective volume after filing with a liquid of between about 30% and about 80% and the strength of said frangible seal is between about 30 inches of water and about 80 inches of water when tested according to ASTM test F1140-07 (2007).

60. The container according to claim 59, wherein said baffle is adapted to provide an effective volume after filing with a liquid of between about 40% and about 70% and the strength of said frangible seal is between about 40 inches of water and about 70 inches of water when tested according to ASTM test F1140-07 (2007).

61. The container according to claim 60, wherein said baffle is adapted to provide an effective volume after filing with a liquid of between about 30% and about 65% and the strength of said frangible seal is between about 45 inches of water and about 65 inches of water when tested according to ASTM test F1140-07 (2007).

62. The container according to claim 60, wherein said baffle is adapted to provide an effective volume after filing with a liquid of about 60% and the strength of said frangible seal is about 55 inches of water when tested according to ASTM test F1140-07 (2007).

\* \* \* \* \*

UNITED STATES PATENT AND TRADEMARK OFFICE
CERTIFICATE OF CORRECTION

PATENT NO. : 10,696,466 B2
APPLICATION NO. : 16/081177
DATED : June 30, 2020
INVENTOR(S) : Whitmore B. Kelley, Jr. et al.

Page 1 of 1

It is certified that error appears in the above-identified patent and that said Letters Patent is hereby corrected as shown below:

In the Claims

In Column 11, Line 56, --RE welding-- should read "RF welding"

Signed and Sealed this
Twenty-fifth Day of August, 2020

Andrei Iancu
*Director of the United States Patent and Trademark Office*